(12) United States Patent
Xue et al.

(10) Patent No.: US 6,870,163 B1
(45) Date of Patent: Mar. 22, 2005

(54) FERROELECTRIC LIQUID CRYSTAL DEVICES USING MATERIALS WITH A DE VRIES SMECTIC A PHASE

(75) Inventors: Jiuzhi Xue, Broomfield, CO (US); David M. Walba, Boulder, CO (US)

(73) Assignee: Displaytech, Inc., Longmont, CO (US)

( * ) Notice: Subject to any disclaimer, the term of this patent is extended or adjusted under 35 U.S.C. 154(b) by 398 days.

(21) Appl. No.: 09/653,437

(22) Filed: Sep. 1, 2000

Related U.S. Application Data
(60) Provisional application No. 60/151,974, filed on Sep. 1, 1999.

(51) Int. Cl.[7] ............................................. G01N 21/19
(52) U.S. Cl. ..................................................... 250/341.1
(58) Field of Search ....................................... 250/341.1

(56) References Cited

U.S. PATENT DOCUMENTS

| | | | |
|---|---|---|---|
| 4,367,924 A | 1/1983 | Clark et al. | 350/334 |
| 4,886,619 A | 12/1989 | Janulis | 252/299.1 |
| 5,062,691 A | 11/1991 | Tristani-Kendra et al. | 359/56 |
| 5,082,587 A | 1/1992 | Janulis | 252/299.01 |
| 5,110,497 A | 5/1992 | Suzuki et al. | 252/299 |
| 5,169,556 A | 12/1992 | Mochizuki | 252/299.62 |
| 5,254,747 A | 10/1993 | Janulis | 568/650 |
| 5,262,082 A | 11/1993 | Janulis et al. | 252/299.01 |
| 5,275,757 A | 1/1994 | Mineta et al. | 252/299.61 |
| 5,322,639 A | 6/1994 | Kawabata et al. | 252/299.62 |
| 5,327,273 A | 7/1994 | Beresnev et al. | 359/104 |
| 5,340,498 A | 8/1994 | Arai et al. | 252/299.65 |
| 5,346,646 A | 9/1994 | Kawabata et al. | 252/299.62 |
| 5,348,685 A | 9/1994 | Mochizuki et al. | 252/299.62 |
| 5,352,379 A | 10/1994 | Nishiyama et al. | 252/299.62 |
| 5,367,391 A | 11/1994 | Johno et al. | 359/56 |
| 5,374,375 A | 12/1994 | Yui et al. | 252/299.65 |
| 5,377,033 A | 12/1994 | Radcliffe | 359/75 |
| 5,378,396 A | 1/1995 | Yui et al. | 252/299.65 |
| 5,389,287 A | 2/1995 | Nishiyama et al. | 252/299.01 |
| 5,399,291 A | 3/1995 | Janulis et al. | 252/299.01 |
| 5,399,701 A | 3/1995 | Janulis | 546/298 |
| 5,417,883 A | 5/1995 | Epstein et al. | 252/299.01 |

(List continued on next page.)

FOREIGN PATENT DOCUMENTS

| | | | |
|---|---|---|---|
| EP | 255236 B1 | 5/1994 | C09K/19/20 |
| EP | 425304 B1 | 7/1996 | G02F/1/137 |
| EP | 579545 B1 | 3/1997 | G02F/1/1337 |
| EP | 736078 B1 | 6/1998 | C09K/19/04 |
| JP | 01213390 A | 8/1989 | C09K/19/46 |
| JP | 01316339 A | 12/1989 | C07D/43/20 |
| JP | 01316367 A | 12/1989 | C07D/239/26 |
| JP | 01316372 A | 12/1989 | C07D/319/06 |
| JP | 8082778 A | 3/1996 | G02F/1/13 |
| JP | 01228128 A | 8/2000 | H01H/12/04 |
| WO | WO 91/00897 A1 | 1/1991 | C09K/19/34 |
| WO | WO 97/36908 A1 | 10/1997 | C07F/7/21 |
| WO | WO 99/33814 A1 | 7/1999 | C07D/239/26 |
| WO | WO 00/31201 A1 | 6/2000 | C09K/19/04 |

OTHER PUBLICATIONS

US 6,030,547, 2/2000, Hasegawa et al. (withdrawn)

Arnett, K.E.et al., "Technique For Measuring Electronic–Based Electro–Optic Coefficients of Ferroelectric Liquid Crystals" (1995), *Mat. Res. Soc. Symp. Proc.* 392:135–146.

(List continued on next page.)

*Primary Examiner*—Constantine Hannaher
(74) *Attorney, Agent, or Firm*—Greenlee, Winner and Sullivan, P.C.

(57) ABSTRACT

Bistable and analog FLC devices employing chiral nonracemic liquid crystal materials exhibiting de Vries smectic A phases. The invention provides certain liquid crystal material that can be employed in both bistable and analog device configurations. The invention also provides a method for identifying liquid crystal materials that will exhibit both bookshelf structure in SSFLC cells and provide V-shaped switching in an analog device configuration.

9 Claims, 6 Drawing Sheets

U.S. PATENT DOCUMENTS

| | | | |
|---|---|---|---|
| 5,437,812 A | 8/1995 | Janulis et al. | 252/299.01 |
| 5,455,697 A | 10/1995 | Coles et al. | 359/103 |
| 5,474,705 A | 12/1995 | Janulis et al. | 252/299.01 |
| 5,482,650 A | 1/1996 | Janulis et al. | 252/299.01 |
| 5,498,368 A | 3/1996 | Coles | 252/294.67 |
| 5,529,718 A | 6/1996 | Hornung et al. | 252/299.61 |
| 5,534,190 A | 7/1996 | Johno et al. | 252/299.65 |
| 5,543,078 A | 8/1996 | Walba et al. | 252/299.65 |
| 5,547,604 A | 8/1996 | Coles et al. | 252/299.01 |
| 5,568,299 A | 10/1996 | Yoshihara et al. | 359/100 |
| 5,583,682 A | 12/1996 | Kitayama et al. | 349/172 |
| 5,595,682 A | 1/1997 | Goodby et al. | 252/299.01 |
| 5,658,491 A | 8/1997 | Kistner et al. | 252/299.01 |
| 5,660,762 A | 8/1997 | Ito et al. | 252/299.67 |
| 5,695,683 A | 12/1997 | Takeichi et al. | 252/299.61 |
| 5,702,637 A | 12/1997 | Johnson et al. | 252/299.61 |
| 5,719,653 A | 2/1998 | Minato et al. | 349/156 |
| 5,723,069 A | 3/1998 | Mineta et al. | 252/299.67 |
| 5,728,864 A | 3/1998 | Motoyama et al. | 560/59 |
| 5,748,164 A | 5/1998 | Handschy et al. | 345/89 |
| 5,750,214 A | 5/1998 | Ito et al. | 428/1 |
| 5,770,108 A | 6/1998 | Totani et al. | 252/299.61 |
| 5,808,800 A | 9/1998 | Handschy et al. | 359/630 |
| 5,827,448 A | 10/1998 | Konuma et al. | 252/299.61 |
| 5,855,812 A | 1/1999 | Radcliffe et al. | 252/299.01 |
| 5,855,813 A | 1/1999 | Coles et al. | 252/299.5 |
| 5,856,815 A | 1/1999 | Mochizuki et al. | 345/97 |
| 5,858,273 A | 1/1999 | Asaoka et al. | 252/299.4 |
| 5,861,108 A | 1/1999 | Ishida et al. | 252/299.62 |
| 5,861,109 A | 1/1999 | Goodby et al. | 252/299.65 |
| 5,888,420 A | 3/1999 | Sakai et al. | 252/299.01 |
| 5,922,242 A | 7/1999 | Saishu et al. | 252/299.62 |
| 5,928,562 A | 7/1999 | Kistner et al. | 252/299.6 |
| 5,936,689 A | 8/1999 | Saishu et al. | 349/123 |
| 5,938,973 A | 8/1999 | Motoyama et al. | 252/299.65 |
| 5,942,155 A | 8/1999 | Coles et al. | 252/299.64 |
| 5,943,112 A | 8/1999 | Mochizuki et al. | 349/173 |
| 5,949,391 A | 9/1999 | Saishu et al. | 345/50 |
| 5,951,914 A | 9/1999 | Matsumoto et al. | 252/299.67 |
| 5,968,413 A | 10/1999 | Mine et al. | 252/299.65 |
| 5,972,241 A | 10/1999 | Johnson et al. | 252/299.61 |
| 5,972,243 A | 10/1999 | Mine et al. | 252/299.65 |
| 5,976,409 A | 11/1999 | Mineta et al. | 252/299.65 |
| 5,980,780 A | 11/1999 | Motoyama et al. | 252/299.64 |
| 5,985,172 A | 11/1999 | Motoyama et al. | 252/299.64 |
| 6,001,278 A | 12/1999 | Matsumoto et al. | 252/299.65 |
| 6,002,042 A | 12/1999 | Mine et al. | 560/66 |
| 6,007,737 A | 12/1999 | Nishiyama et al. | 252/299.01 |
| 6,018,070 A | 1/2000 | Ito et al. | 560/76 |
| 6,019,911 A | 2/2000 | Hirano et al. | 252/299 |
| 6,045,720 A | 4/2000 | Shundo et al. | 252/299.61 |
| 6,051,639 A | 4/2000 | Mehl et al. | 524/205 |
| 6,057,007 A | 5/2000 | Amano et al. | 428/1 |
| 6,084,649 A | 7/2000 | Amano et al. | 349/96 |

OTHER PUBLICATIONS

Blinov L.M.and Tournilhac, F., "Infra–Red Dichroism of Mesophases Formed by Polyphilic Molecules. 1. Development of the Technique and Study of Compounds With One Long Perfluorinated Tail" (1993), *Molecular Materials,* 3(1):93–111.

Booth, C.J. et al., "The ferro–,ferri– and antiferro–electric properties of a series of novel 2– or 3–substutited–alkyl4–(4'–dodecyloxybiphenyl–4–carbonyloxy)–benzoate esters" (1996), *Liquid Crystals* 20(6):815–823.

Booth, C.J. et al., "Achiral swallow–tailed materials with 'antiferroelectric–like' structure and their potential use in antiferroelectric mixtures" (1996), *Liquid Crystals* 20(4):387–392.

Chandani, A.D. et al., "Novel Phases Exhibiting Tristable Switching" (Jul. 1989), *Jpn. J. App. Phys.* 28:L1261–1264.

Chandani, A.D. et al., "Antiferroelectric Chiral Smectic Phases Responsible for the Tristable Switching in MHPOBC" (Jul. 1989), *Jpn. J. App. Phys.* 28:L1265–1268.

Chandani, A.D. et al., "Tristable Switching in Surface Stabilized Ferroelectric Liquid Crystals with a Large Spontaneous Polarization" (May 1988), *Jpn. J. App. Phys.* 27(5):L729–L732.

Clark, N.A. and Lagerwall, S.T., "Submicrosecond bistable electro–optic switching in liquid crystals" (Jun. 1980), *Appl. Phys. Lett.* 36:899.

Dawson, D.J. et al., "Cocyclotrimerization of Aryl Acetylenes: Substituent Effects on Reaction Rate" *Am. Chem. Soc. Sym.* 346 Ch 38:446–456.

de Vries, A., "Experimental Evidence Concerning Two Different Kinds Of Smectic C To Smectic A Transitions" (1977), *Mol. Cryst. Liq. Cryst. (Letters )* 41:27–31.

de Vries, A., "The Implications of the Diffuse–Cone Model for Smectic A and C Phases and A–C Phase Transitions" (1979), *Mol. Cryst. Liq. Cryst (Letter).* 49:179–185.

Drzewinski, W. et al. "Antiferroelectric Liquid Crystals with Fluorinated Parts of Terminal Chains" CAPLUS 1998:624787.

Edgar, K. J. and Falling, S.N., "An Efficient and Selective Method for the Preparation of Iodophenols" (1990) *Org. Chem.* 55:5287–5291.

Fleming, F. F. and Jiang, T., "Unsaturated Nitriles: Optimized Coupling of the Chloroprene Grignard Reagent[1] with w–Bromonitriles" *J.Org. Chem.* (1997) 62:7890–7891.

Gorecka, E. et al., "Molecular Orientational Structures in Ferroelectric, Ferrielectric and Antiferroelectric Smectic Liquid Crystal Phases as Studied by Conoscope Observation" (Jan. 1990), *Jap. J. App. Phys.* 29(1):L131–L137.

Hartmann, W., "Uniform SSFLC Director Pattern Switching" (1988), *Ferroelectrics* 85:67–77.

Heinemann, S. et al., "Synthesis and Dielectric Investigations of New Swallow–Tailed Monomers and Polymers" (1993), *Mol. Cryst. Liq. Cryst.* 237:277–283.

Heinemann, S. et al., "Competition between dipolar and steric interactions in swallow–tailed compounds" (1993), *Liquid Crystals* 13(3):373–380.

Hide, F. et al., "Dynamic Polarized Infrared Spectroscopy of Electric Field–Induced Molecular Reorientation in a Chiral Smectic–A Liquid Crystal" (Sep. 1995), *Phys. Rev. Lett.* 75:2344–2347.

Inui, S. et al., "Thresholdless antiferroelectricity in liquid crystals and its application to displays" (1996), *J. Mater. Chem.* 6(4):671–673.

Johno, M. et al., "Correspondence between Smectic Layer Switching and DC Hysteresis of Apparent Tilt Angle in an Antiferroelectric Liquid Crystal Mixture" (Jan. 1990)), *Jap. J. Applied. Phys.* 29:L111–114.

Johno, M. et al., "Smectic Layer Switching by an Electric Field in Ferroelectric Liquid Crystals Cells" (Jan. 1989), *Jpn. J. App. Phys.* 28:L119–120.

Kagawa, A. et al., "Fast Response Time STN=LCD with High Contrast Ratio" (*1995*), *Proceedings of the 15th International Display Research Conference* 177–180.

Klöpper et al., "IR–Modulation Spectroscopy on the Collective Dynamics of Free–Standing Ferroelectric Liquid Crystalline Films" (Jan. 1997), *J. Physique II* 7(1):57–67.

Matsumoto, T. et al., "A novel property caused by frustration between ferroelectricity and antiferroelectricity and its application to liquid crystal displays—frustoelectricity and V–shaped switching" (Sep. 1999) *J. Mater. Chem.* 9:2051–2080.

Mikami, D. et al., "Binaphthol–Titanium Complex–Catalyzed Fluoral–Ene Reaction with Vinyl Sulfides for Asymmetric Synthesis of Diastereomeric a Trifluoromethyl–b–methyl Carbinols: Diastereomer Switch of Antiferroelectric or Ferroelectric Properties of Diastereomeric Liquid–Crystalline Systems[1]" (Sep. 1996).

Mochizuki, A. et al., "A High Contrast and High Transmittance Multiplexing SSFLC Display Utilizing Naphthalene Base Liquid Crystal Materials" (1991), *Ferroelectrics* 122:37–51.

Mottram, N.J. and Elston, S.J., "Preliminary communication Thresholdless switching induced by polar anchoring in antiferroelectric liquid crystals" (1999) *Liquid Crystals* 26(12):1853–1856.

Nakagawa, A., A Hysteresis Model for Antiferroelectric $SmC_{A*}$ (Aug. 1991), *Jap. J. App. Phys.* 30:L1759–1764.

Ostrovskii, B.I. et al., "Evidence of Tilted Dimeric Mesophase for Terminally Polar Polyphilic Mesogens" (1995), *J. Physique II* 5(7):979–1001.

Park, B. et al., "Molecular motion in a smectic liquid crystal showing V–shaped switching as studied by optical second–harmonic generation"(Apr. *1999*) *Physical Review E* 59(4) 3815–3818.

Perova, T.S. et al., "Study Of The Molecular Orientation In A Chiral Smectic Liquid Crystal Mixture using Infrared Dichroism" (1996), *Ferroelectrics* 180(1–4):105–115.

Redmond, M. et al., "Ferroelectric and Electroclinic Characterisation of a New Organic Siloxane Bimesogen." (1992)*Ferroelectrics* 148:323–336.

Rieker, T.P. et al., ""Chevron" Local Layer Structure in Surface–Stabilized Ferroelectric Smectic–C Cells" (Dec. 1987), *Physical Rev. Letts.* 59(23):2658–2661.

Rudquist, J.P. et al., "The case of thresholdless antiferroelectricity: polarization–stabilized twisted SmC* liquid crystals give V–shaped electro–optic response" (1999), *J. Mater. Chem.* 9:1257–1261.

Sakaigawa, A. and Nohira, H., "Properties of Ferroelectric Liquid Crystal Mixtures Containing Fluorine Substituted Compounds" (1993) *Ferroelectrics* 148:71–78.

Schmitt, K. et al., "Strongly non–linear optical ferroelectric liquid crystals for frequency doubling" (1993) *Liquid Crystals,* 14(6): 1735–1752.

Seomun, S.S. et al., "Evolution of Switching Characteristics from Tristable to V–Shaped in an Apparently Antiferroelectric Liquid Crystal" (Jun. 1997), *Jpn. J. App. Phys.* 36:3586–3590.

Takanishi, Y. et al., "Spontaneous Formation of Quasi–Bookshelf Layer Structure in New Ferroelectric Liquid Crystals Derived from a Naphthalene Ring" (Jun. 1990), *Jap. J. Applied Phys.* 29(6):L984–L986.

Zhuang, Z., "Interfacial Interactions, Director Configurations and Layer Structures of Surface Stabilized Ferroelectic Liquid Crystals" (1991), *Ph.D. Thesis University of Colorado, Boulder CO.* 105 pages.

Tuffin, R.P. et al., "Non–Chiral Compounds Exhibiting Alternating Tilt Smectic Phases," *Mol. Cryst. Liq. Cryst.* 1995, 260:51–67.

FERROELECTRIC LIQUID CRYSTAL DEVICES USING MATERIALS WITH A DE VRIES SMECTIC A PHASE

CROSS-REFERENCE TO RELATED APPLICATIONS

This application takes priority under 35 U.S.C. 119(e) from U.S. provisional application Ser. No. 60/151,974, filed Sep. 1, 1999 which is incorporated by reference herein in its entirety to the extent that it is not inconsistent herewith.

BACKGROUND OF THE INVENTION

This application relates generally to electrooptical devices and liquid crystal materials employed in such devices. More particularly, the invention relates to bistable and analog electrooptical devices employing ferroelectric liquid crystal materials.

Liquid crystals have found use in a variety of electrooptical and display device applications, in particular those which require compact, energy-efficient, voltage-controlled light valves such as watch and calculator displays.

Thermotropic liquid crystal molecules typically possess structures which combine a rigid core coupled with two relatively "floppy" tails. Such LC molecules are generally rod-like in shape with the rigid core generally along the long axis of the molecule. Ferroelectric liquid crystal (FLC) materials have been prepared by the introduction of one or more chiral nonracemic LC molecules having one or more stereocenters in at least one of the tails to introduce chirality. The first FLC compound to be characterized was DOBAMBC which contains an (S)-2-methylbutyloxy chiral tail. Pure DOBAMBC exhibits a smectic $C^*$ phase with a ferroelectric polarzation of −3 $nC/cm^2$.

Electro-optic effects with sub-microsecond switching speeds can be achieved using the technology of N. A. Clark and S. T. Lagerwall (1980) Appl. Phys. Lett. 36:899 and U.S. Pat. No. 4,367,924. These investigators have reported display structures using FLC materials, the so-called Surface-Stabilized FLC (SSFLC) devices, having not only high speed, but which also exhibit bistable, threshold sensitive switching. Such properties make FLC-based devices excellent candidates for light modulation devices including matrix addressed light valves containing a large number of elements for passive displays of graphic and pictorial information, optical processing applications, as well as for high information content dichroic displays.

It is, however, well known in the art of FLC materials and devices that a typical FLC device does not exhibit true optical bistability, that is, the memory or the zero applied field orientation of the optic axis of the SSFLC device is typically different from that of its driven orientation. Descriptions of the construction and operation of a conventional bistable FLC device can be found, for example, in U.S. Pat. Nos. 5,748,164 and 5,808,800. The FLC materials used in these conventional devices exhibit smectic layer spacing shrinkage at the smectic A to smectic C transition and further into the smectic C phase. The most significant consequence of the decrease in smectic layer thickness, is the formation of chevron smectic layer structures. In addition to inducing many defects, formation of such chevron structures, in effect, adds an extra interface at the chevron interface which is a nominally planar interface roughly parallel to the plane of the FLC film. This extra interface is internal to FLC materials, and together with the two surfaces bounding the FLC materials and the external electric field, determines the orientation of the optic axis of the FLC device. The added constraint imposed by the chevron interface is that the orientation of the optic axis of the FLC devices under an applied electric field depends on the strength of the applied field, and is, thus, different from the memory orientation of the device in the absence of the applied field.

FIG. 1A illustrates a smectic $C^*$ chevron interface. See, for example, Rieker, T. et al. (1987) Physical Rev. Letts. 59(23):2658 for a discussion of chevron layer structure in SSFLC cells. FIG. 2A schematically illustrates a typical electrooptical response (output light intensity as a function of applied voltage) of a conventional bistable FLC device. This conventional bistable device does not exhibit a true bistable switching and does not exhibit analog behavior. FLC compositions exhibiting bookshelf geometry (FIG. 1B) will, in contrast, be substantially chevron-free when aligned in SSFLC devices and exhibit true bistable electrooptical response as schematically illustrated in FIG. 2B.

Much attention has focused on the construction of FLC electrooptical devices with true optically bistability which are extremely desirable in practical applications to achieve stable memory performance, high contrast ratio, wide viewing angle and high speed response. However, only a few FLC materials have been identified which exhibit true bistability. A small class of naphthalene-based LCs were reported to be useful for preparation of FLC mixtures exhibiting optical bistability (Mochizuki et al. (1991) Ferroelectrics 122:37–51, U.S. Pat. No. 5,169,556, EP published application 405,868 (published Feb. 1, 1991) and U.S. Pat. No. 5,348,685.) These FLC materials are said have bookshelf geometry and to exhibit no smectic layer spacing shrinkage at the smectic A (SmA) to the chiral smectic C (SmC*) transition and into the SmC* phase range, unlike many conventional FLC materials. U.S. Pat. Nos. 5,568,299, 5,856,815 and 5,943,112 report applications of the naphthalene-based FLCs of U.S. Pat. Nos. 5,169,556 and 5,348,685.

Additional naphthalene-core LCs are reported to provide improvement in response times and/or temperature dependency of response time in U.S. Pat. No. 5,861,108. While this patent discloses numerous naphthalene-core LC molecules and LC molecules with related structures, it does not indicate that any of the disclosed LC molecules provide chevron-free bistable FLCs.

U.S. Pat. Nos. 5,262,082, 5,437,812 and 5,482,650 report achiral LC compounds having perfluoroether terminal groups exhibiting smectic phases or latent smectic phases that are said to provide "reduced temperature dependence of the smectic interlayer spacing" and "spontaneous generation of a bookshelf layer structure ideal for a ferroelectric liquid crystal device." Preferred chiral LCs of these patents have a phenylpyrimidine core. A number of LC molecules have been reported to be useful in combination with these achiral bookshelf LCs.

U.S. Pat. Nos. 5,474,705, 5,702,637 and 5,972,241, as well as published EP application EP 736,078 (published Jun. 24, 1998) report chiral LC compounds also having a perfluoroether terminal portion or a chiral fluorinated terminal portion with preferred LC compounds having phenylpyrimidine cores. These patents report that the chiral LC molecules disclosed can be admixed with the achiral fluoroether-containing compounds of U.S. Pat. Nos. 5,262,082, 5,437,812 and 5,482,650 to exhibit "reduced temperature dependence of the smectic interlayer spacing" and "spontaneous generation of a bookshelf layer structure ideal for a ferroelectric liquid crystal device.

U.S. Pat. Nos. 5,658,491, 5,855,812 and 5,928,562 report a process for controlling cone tilt angle in tilted smectic FLC compositions. The compounds disclosed contain fluoroether or fluoroalkyl groups in the LC tail. The patents further report that the compounds useful in the invention can be admixed with the achiral fluoroether-containing compounds of U.S. Pat. Nos. 5,262,082, 5,437,812 and 5,482,650 to exhibit "reduced temperature dependence of the smectic interlayer spacing" and "spontaneous generation of a bookshelf layer structure."

U.S. Pat. Nos. 4,886,619, 5,082,587, 5,399,291, 5,399,701 report chiral and achiral LC molecules having tilted smectic mesophases or latent tilted smectic mesophases and having fluorocarbon terminal portions. The LC compounds disclosed have structural features in common with bookshelf LCs of U.S. Pat. Nos. 5,262,082, 5,437,812 and 5,482,650, however, none of the LC compounds disclosed are specifically identified as useful for preparation of chevron-free bistable FLCs.

U.S. Pat. Nos. 5,750,214 and 5,858,273 report liquid crystal devices with certain alignment control, which is said to be useful in improving a switching characteristic of a chiral smectic liquid crystal composition having bookshelf structure. The patents refer to the use of FLC compositions in the method in which at least one component of the FLC composition has a fluorocarbon terminal portion. The patents refer specifically to the use of compounds of bookshelf LCs of U.S. Pat. No. 5,262,082.

U.S. Pat. Nos.6,019,911 and 6,007,737 report various liquid crystal compositions having structures related to the naphthalene and phenyl pyrimidines that are noted above to exhibit spontaneous generation of bookshelf structure. However, none of the LC compounds disclosed in these patents is identified as exhibiting bookshelf structure or as useful in the preparation of chevron-free FLCs.

In the field of analog FLC devices, a so-called 'V-shaped' switching has been reported in a class of FLCs known to produce antiferroelectric phases. Antiferroelectric LCs (Chandani et al. (1988) Jpn. J. App. Phys. 27(5):L729–L732) exhibit three stable states and are characterized by a distinct threshold and double hysteresis that generates a memory effect in the driven states. A typical electrooptic response of an antiferroelectric LC is schematically illustrated in FIG. 3A and a V-shaped switching response is schematically illustrated in FIG. 3B.

V-shaped switching is a thresholdless (or low threshold), hysteresis-free (or low hysteresis) switching effect that was first reported by Fukuda A. (1995) Asia Display'95, Proceedings of the 15$^{th}$ International Display Research Conference 61:177 and by Inui et al. (1996) J. Mater. Chem. 6:671 in a three component antiferroelectric LC mixture of compounds A:B:C (40:40:20 mass %) see Scheme 1, where * indicates an asymmetric carbon. It was later reported by Seong et al. (1997) J. Appl. Phys. 36:3586–3590 that compound A in this mixture when homogeneously aligned in an LC cell exhibited V-shaped switching in an antiferroelectric phase at certain temperatures. The only known test of V-shaped switching is the actual observation of the high susceptibility analog effect in FLC cells.

A "Thresholdless" antiferroelectric effect has been reported by some researchers (Fukuda, A. (1995) Asia Display '95 Proceedings of the 15$^{th}$ Int'l Display Research Conference 61:177 and Inui, S. et al. (1996) J. Mater. Chem 6:671) and a "ferrielectric" effect by yet other researchers (E. Gorecka et al. (1990) Jap. J. Appl. Physics 29(1):L131-L-137; Booth et al. (1996) Liquid Crystals 20(6):815–823). These effects have also been associated with antiferroelectric LC molecules. It is believed that both of these effects are substantially the same a V-shaped switching.

U.S. Pat. No. 5,942,155 reports a siloxane LC molecule that exhibits an antiferroelectric LC phase having little or no hysteresis and low threshold voltage.

U.S. Pat. Nos. 6,057,007, 6,084,649, WO 99/33814 (published Jul. 8, 1999) and WO 00/31210 (Published Jun. 2, 2000) report tristable liquid crystal devices comprising a titled smectic or induced tilted smectic LC composition. Many of the LC molecules specifically exemplified have phenylpyrimidine cores and a chiral (U.S. Pat. No. 6,057,007) or achiral (U.S. Pat. No. 6,084,649) terminal fluorocarbon group. Compositions disclosed are reported to exhibit low threshold, low hysteresis switching "approaching the ideal 'V-shaped' switching. However, data presented in the listed U.S. patents (specifically in Table 2) report only two LCs (both in U.S. Pat. No. 6,057,007) with zero hysteresis. The structures of the phenylpyrimidine LC molecules reported to exhibit no hysteresis on switching are illustrated in Scheme 2.

The ferrielectric effect was first reported in 4-(1-methylheptyoxycarbonyl)phenyl-4-(4'-octyloxybiphenyl) carboxylate (MHPOBC) by Gorecka, E. et al. (1990) supra. Booth wt al. (1996) Liquid crystals 20(6):815–823 also report ferrielectric LCs.

U.S. Pat. No. 5,728,864 reports certain chiral LCs having ferrielectric phases comprising a chiral ester tail group of structure:

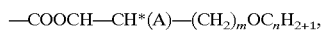

where * indicates an asymmetric carbon, A can be —CF$_3$, or —C$_2$F$_5$, and m and n are integers ranging from 2–4. The structure of the disclosed ferrielectric LC is given in Scheme 3.

U.S. Pat. No. 6,002,042 reports chiral "swallow-tailed" LC compounds illustrated in Scheme 4 with a trifluoromethyl substituted chiral tail group which have an antiferroelectric phases or ferrielectric phase showing V-shaped optical response.

U.S. Pat. Nos. 6,001,278, 5,938,973 and 5,976,409 report achiral swallow-tailed LC compounds that can be combined with chiral ferrielectric LC compounds to obtain ferrielectric LCs exhibiting V-shaped optical response. The swallow-tailed LC compounds disclosed have one branched alkyl ester tail with various benzoate, and phenyl benzoate cores with 1–3 phenyl rings, which may be substituted at certain ring positions with halides (particularly fluorines) see Scheme 5. Swallow-tailed LCs are also reported by Heinemann, S. et al. (1993) Mol. Cryst. Liq. Cryst. 237:277–283, Heinemann, S. et al. (1993) Liquid Crystals 13(3):373–380 and Booth, C. J. et al. (1996) Liquid Crystals 20(4): 387–392.

U.S. Pat. Nos. 5,340,498, 5,985,172, 5,980,780, 6,001,278, and 6,018,070 variously report chiral and achiral LC molecules that are said to be useful in the formation of antiferroelectric LCs. LC compounds of these patents have an ester tail of formula:

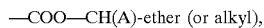

where A can variously be H, —CF$_3$, —CH$_3$, or —C$_2$H$_5$ (dependent upon the structure of the rest of the molecule) and the carbon of the —CH(A)— moiety can be chiral. The tail group is similar in structure to chiral tail groups of ferrielectric LCs. However, these patents do not specifically report the presence of any of V-shaped switching, ferrielectric effect or thresholdless antiferroelectric effect in any of the disclosed compounds.

Antiferroelectric LCs are also reported in the following references: JP-A-1-213390, JP-A-1-316339, JP-A-1-316367, JP-A-1316372, JP-A-2-28128, (1989) Liquid Crystals 6:167, Chandani et al. (1988) Jap. J. Applied Physics 27:L729–732, Chandani et al. (1989) Jap. J. Applied Physics 28:L1261–1264, Chandani et al. (1989) Jap. J. Applied Physics 28:L1265–1268, Chandani et al. (1989) Jap. J. Applied Physics 28:L119–120, Johno et al. (1990) Jap. J. Applied Physics 29: L111–114, Nakagawa A. (1991) Jap. J. Applied Physics 30:L1759–1564.

Liquid crystal compounds and compositions that exhibit bookshelf structure useful in constructing electrooptical devices with true bistable optical response or that exhibit V-shaped switching (low or no threshold and low or no hysteresis) useful in constructing analog electrooptical devices are of significant interest in the field. Liquid crystals currently known in the art to exhibit these desirable electrooptical properties represent a relatively narrow range of chemical structures. It is of great interest in the art to expand the range of structures of liquid crystals compounds that exhibit true bistable optical response or V-shaped switching to facilitate additional improvements in other desirable properties of materials and adaptation of materials for use in different applications. Properties that it would be desirable to improve or control include, among others, chemical (including photochemical) stability, viscosity, compatibility with other liquid crystal compounds to form mixtures, wide and useful operating temperature range, tilt angle, switching speed, spontaneous polarization, and birefringence.

SUMMARY OF THE INVENTION

The present invention provides electrooptical devices that exhibit true bistable response and devices that exhibit low threshold, low hysteresis V-shaped switching analog response. The devices of this invention contain a liquid crystal material that has a de Vries smectic A phase. The invention also provides a method for identifying a liquid crystal material for use in either type of electrooptical device by assessing the liquid crystal material for the presence of a de Vries smectic A phase. The presence of a de Vries smectic A phase in a selected liquid crystal material can be assessed using infrared dichroism as described herein.

The invention is based on the discovery that a chiral non-racemic liquid crystal material (compounds or mixtures of compounds) that exhibits a de Vries Smectic A phase will exhibit a true bistable response or a low threshold, low hysteresis V-shaped switching response when the liquid crystal is introduced into a liquid crystal cell configuration appropriate for obtaining the respective bistable and analog optical responses.

The invention specifically relates to methods for identifying chiral nonracemic compounds or liquid crystals that are mixtures of chiral and achiral or racemic liquid crystals that are useful in the preparation of liquid crystal materials for true bistable response by detecting or assessing the presence of a de Vries smectic A phase in the compound or compound mixtures. The invention further relates to methods for making an electrooptic device that exhibits true bistable response by providing a chiral nonracemic liquid crystal material exhibiting a de Vries smectic A phase. The chiral nonracemic liquid crystal material exhibiting the de Vries smectic A phase can comprises one or more chiral nonracemic, achiral or nonracemic liquid crystal compounds that each exhibit a de Vries smectic A phase. The chiral nonracemic liquid crystal material exhibiting the de Vries smectic A phase can comprise components that do not themselves exhibit the de Vries smectic A phase, but which do not significantly adverse affect the formation of that phase.

More specifically, the method of the present invention can be applied to assess the presence of a de Vries Smectic A phase in selected classes of known liquid crystal compounds or materials that have been identified as exhibiting V-shaped switching. The identification of the presence of the de Vries Smectic A phase demonstrates that the known liquid crystal compound or material can be employed in the construction of a true bistable device.

In particular, the method can be applied to any liquid crystal material or compound that has been identified as exhibiting V-shaped switching, ferrielectric effect or thresholdless antiferroelectric effect. Generally, the method is applicable to any liquid crystal material or liquid crystal compound that has been identified as an antiferroelectric liquid crystal or as useful as a component in an antiferroelectric liquid crystal. Further, the method can be applied to liquid crystals containing certain structural features common to liquid crystals that exhibit an antiferroelectric effect or more specifically that exhibit V-shaped switching, a ferrielectric effect or a thresholdless antiferroelectric effect. The method is particularly applicable to liquid crystal compounds comprising, among others:

1-methyl alkoxy chiral tails, 1-ethyl alkoxy chiral tails, 1-trifluoromethylalkoxy chiral tails, 1-pentafluoroethlyalkoxy chiral tails and more particularly LCs with phenyl pyrimidine cores, biphenyl benzoate or phenyl benzoate cores comprising these tails;

—COO—CH(A)-ether (or alkyl, fluoroether, or fluoroalkyl), where A can be —CF$_3$, —C2F5, —CH$_3$, or C$_2$H$_5$ and the tail is chiral nonracemic, achiral or racemic and particularly LCs with phenyl pyrimidine cores, biphenyl benzoate or phenyl benzoate cores comprising these tails;

a chiral or achiral terminal fluorocarbon group, such as exemplified in U.S. Pat. Nos. 6,057,007 and 6,084,649, and particularly LCs with phenyl pyrimidine cores, biphenyl benzoate or phenyl benzoate cores comprising these tails;

swallow-tailed liquid crystals; and naphthalene-core LC molecules and LC molecules as described in U.S. Pat. No. 5,861,108.

Further, the method can be applied to classes of known liquid crystal compounds which have not been identified as useful in true bistable devices but, which have structural features the same as or related to those commonly found in liquid crystals that have been identified as exhibiting bookshelf geometry and true bistability. For example, the method can be applied to any liquid crystal (chiral nonracemic, achiral or racemic) which has a naphthalene-containing core or a core derived from naphthalene, such as cores containing dehydronaphthalenes.

True bistable FLC electrooptical devices of this invention include those which comprise FLCs that exhibit de Vries Smectic A phases and in which at least one component of the FLC comprises a chiral nonracemic, achiral or racemic tail and/or a LC core selected from:

1-methyl alkoxy tails, 1-ethyl alkoxy tails, 1-trifluoromethylalkoxy tails, 1-pentafluoroethlyalkoxy tails;

—COO—CH(A)-ether (or alkyl, fluoroether, or fluoroalkyl), where A can be —CF$_3$, —C2F5, —CH$_3$, or C$_2$H$_5$;

a chiral or achiral terminal fluorocarbon group tail, such as exemplified in U.S. Pat. Nos. 6,057,007 and 6,084,649, and particularly those in combination with phenyl pyrimidine cores, biphenyl benzoate or phenyl benzoate cores; chiral nonracemic, achiral and racemic swallow tails of swallow-tailed liquid crystals; and naphthalene-cores or other cores of LC molecules as described in U.S. Pat. No. 5,861,108.

The invention is, however, not intended to encompass a device containing an LC compound or material already known in the art to spontaneously form a bookshelf structure. Many known bookshelf materials are encompassed within references cited herein above. The invention is, however, intended to encompass new combinations of LC compounds which may comprises one or more art-known bookshelf LC compounds where the assays disclosed herein determine that the new combination exhibits a de Vries smectic A phase.

The method of this invention can also be generally applied to any classes of liquid crystal materials that exhibit tilted smectic phases, such as smectic C phases, to determine whether or not the materials possess a de Vries smectic A phase. For example, the method can be applied to LC dimers, twin LC molecules, various siloxane-containing LC materials, including siloxane materials reported in U.S. Pat. No. 5,455,697.

Useful FLCs exhibiting de Vries Smectic A phases include, among others, those with phenyl pyrimidine cores, biphenyl benzoate, biphenyl benzoate, phenyl benzoate cores, naphthalene-cores, dehydronaphthalene cores.

The invention further specifically relates to methods for identifying chiral nonracemic a liquid crystal compounds or liquid crystals that are mixtures of chiral compounds and achiral or racemic that are useful in the preparation of liquid crystal materials for V-shaped switching useful in analog FLC devices by detecting or assessing the presence of a de Vries Smectic A phase in the compound or compound mixtures. The invention further relates to methods for making an electrooptic device that exhibits V-shaped switching by providing a chiral nonracemic liquid crystal material exhibiting a de Vries Smectic A phase. The chiral nonracemic liquid crystal material exhibiting the de Vries Smectic A phase can comprise one or more chiral nonracemic, achiral or nonracemic liquid crystal compounds. The chiral nonracemic liquid crystal material exhibiting the de Vries Smectic A phase can comprise components that do not themselves exhibit the de Vries Smectic A phase, but which do not significantly adversely affect the formation of that phase.

More specifically, the method of the present invention can be applied to assess the presence of a de Vries Smectic A phase in selected classes of known liquid crystal compounds or materials that have been identified as spontaneously forming bookshelf geometry. The identification of the presence of the de Vries Smectic A phase demonstrates that the known liquid crystal compound or material can be employed in the construction of an analog device exhibiting V-shaped switching. In particular, the method can be applied to any liquid crystal material or compound that has been identified as exhibiting bookshelf geometry or that has been identified as useful in the formation of low defect or chevron-free bistable FLC devices. Further, the method can be applied to liquid crystals containing certain structural features common to liquid crystals that spontaneously form the bookshelf geometry. The method is particularly applicable to liquid crystal compounds comprising, among others:

naphthalene-cores, and dehydronaphthalene cores (see Scheme 6);

perfluoroether terminal groups and particularly those which have a phenyl pyrimidine core;

a chiral or achiral terminal fluorocarbon group, such as exemplified in U.S. Pat. Nos. 6,057,007 and 6,084,649, and particularly LCs with phenyl pyrimidine cores, biphenyl benzoate or phenyl benzoate cores comprising these tails;

swallow-tailed liquid crystals; and naphthalene-core LC molecules and other LC molecules as described in U.S. Pat. No. 5,861,108.

True analog FLC electrooptical devices of this invention exhibiting low threshold, low hysteresis V-shaped switching include, among others, those which comprise an FLC that exhibits a de Vries Smectic A phase and in which at least one component of the FLC comprises a chiral nonracemic, achiral or racemic tail and/or a core group selected from, among others:

naphthalene-cores, and dehydronaphthalene cores (see Scheme 6);

perfluoroether terminal groups and particularly those which also have a phenyl pyrimidine core;

a chiral or achiral terminal fluorocarbon group, such as exemplified in U.S. Pat. Nos. 6,057,007 and 6,084,649, and particularly LCs with phenyl pyrimidine cores, biphenyl benzoate or phenyl benzoate cores comprising these tails;

a chiral nonracemic, achiral or racemic swallow tails of a swallowed-tail liquid crystal; and naphthalene-cores LC molecules and other cores of LC molecules as described in U.S. Pat. No. 5,861,108.

The invention is, however, not intended to encompass a device containing an LC compound or material already known in the art to exhibit V-shaped switching. Many known materials that are currently known to exhibit V-shaped switching are encompassed within references cited herein above. The invention is, however, intended to encompass new combinations of LC compounds which may comprises one or more art-known LC compounds that exhibit V-shaped switching where the assays disclosed herein determine that the new combination exhibits a de Vries smectic A phase.

In specific embodiments, the invention provides chiral nonracemic, achiral and racemic liquid crystal compounds of the formulas 8-1 and 8-2 (see Scheme 8) which exhibit a de Vries smectic A phase. These materials are useful in the preparation of FLC materials for use in true bistable chevron-free FLC devices and in true analog devices exhibiting V-shaped switching. The invention specifically provides liquid crystal materials comprising the chiral nonracemic compounds W399 and W415 the structures of which are provided in Scheme 7 as well as the enantiomers and racemates thereof. These compounds both exhibit a de Vries Smectic A phase and are useful in the preparation of FLC materials for true bistable bookshelf devices and true analog devices exhibiting V-shaped switching. Thus, the invention is directed to bookshelf aligned FLCs comprising W399, W415 (or enantiomers thereof) or both, to bistable FLC devices employing bookshelf aligned FLCs comprising W399, W415 (or enantiomers thereof) or both, to V-shaped switching FLC compositions comprising W399, W415 (or enantiomers thereof) or both and to analog FLC devices comprising V-shaped switching compositions comprising W399, W415 (or enantiomers thereof) or both.

This invention provides device constructions and in particular alignment layer conditions for constructing true analog FLC cells with de Vries SmA materials and for constructing bistable FLC cells with de Vries smectic A materials. A number of FLC materials are already known to be bookshelf materials and a number of FLC materials are already known to exhibit V-shaped switching, all as described in the Background of the Invention. It is intended to exclude all materials already known for a given use (either bistable or V-shaped switching) from the claims. Thus, this invention encompassed true bistable SSFLC devices incorporating any FLC materials that exhibit a de Vries smectic A phase, except those FLC materials, such as the naphthalene-core bookshelf materials, that have already been identified and known in the art to form bookshelf geometry in a properly configured SSFLC cell. Similarly, this invention encompasses true analog V-shaped switching devices incorporating any FLC materials that exhibit a de Vries smectic A phase, except those FLC materials, such as certain compounds having fluorocarbon groups in their chiral tails, that have already been identified and known in the art to exhibit V-shaped switching when aligned in an appropriate analog cell device configuration. The invention, is however, intended to encompass new combinations of LC compounds to give new mixtures thereof which may comprise one or more materials that were known in the art to be useful for V-shaped switching or known in the art to form bookshelf geometry in SSFLC cells. The method of this invention is employed to determine the presence of the de Vries smectic A phase in the new composition.

The invention also provides methods for modifying de Vries smectic A materials to enhance the analog or bistable character of devices which use the modified materials. The efficacy of this teaching is very surprising, given that bistabilty and analog switching are known to be at opposite ends of the SSFLC EO behavior spectrum. In fact, those with ordinary skill in the art believe that the observed V-shaped switching and the observed optical bistability are completely distinct phenomena, and they expect these very different behaviors to have very different underlying causes. The present invention, however, shows that they are closely linked and that either behavior can be elicited from a single FLC material via the proper cell construction and alignment layer conditions.

Preferred liquid crystal compounds of this invention are those that exhibit smectic phases or latent smectic phases. Liquid crystal compounds with latent smectic phases are those compounds which do not themselves exhibit the smectic phase, but which in combination with other liquid crystals, which may or may not exhibit any smectic phase, form a mixture which exhibits the smectic phase. Liquid crystal compounds and materials of this invention include those which have no nematic phase. Liquid crystal compounds and materials of this invention include those which have the phase sequence: Isotropic→SmA→SmC or Isotropic→SmA→SmC* with decreasing temperature, where the SmA phase is a de Vries smectic A phase over at least a useful portion (at least about 5° C.) of the temperature range of the Sm A phase.

Liquid crystal materials of this invention are preferably chemically and photochemically stable and have properties such as spontaneous polarization and tilt angle and birefringence appropriate for a selected application. As is known in the art, some applications liquid crystal materials having a tilt angle of about 22.5° C. are preferred. In some application high polarization as is known in the art is preferred and in other application low polarization as is known in the art is preferred. In some applications, low birefringence or negative birefringence LC materials are all preferred to allow thicker LC layers to be employed in selected device application and/or to decrease chromaticity in certain device configuration.

Preferred bistable devices of this invention are those that exhibit contrast ratios greater than about 50:1 or more preferably greater than about 100:1.

Additional features and benefits of the LC materials, devices and methods of this invention will become apparent on review of the following detailed description.

BRIEF DESCRIPTION OF THE DRAWINGS

FIG. 3E illustrates the separated substrates of FIG. 3D to more clearly illustrate rubbing directions.

DETAILED DESCRIPTION OF THE INVENTION

Figure 1A:
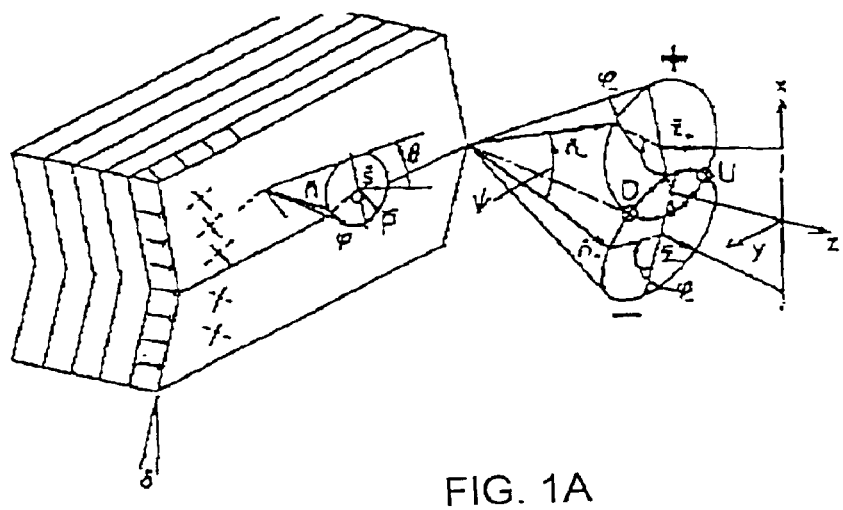
FIG. 1A is a schematic illustration of the chevron layer structure in an SSFLC.

As noted above, an SSFLC device employing conventional FLCs has a chevron FLC layer structure (FIG. 1A) rather than a bookshelf layer structure (FIG. 1B) in which the LC layer is perpendicular to the substrate between which the LC is introduced. As a result of the chevron structure, the SSFLC device exhibits zigzag defects. These defects lead to poor contrast ratio and unstable bistability. In spite of this, SSFLC devices using conventional FLCs are often described as bistable. However, in order to achieve bistable FLC devices, it is necessary to eliminate the chevron interfaces.

W. Hartmann (1988) Ferroelectrics, Vol. 85, 67–77 reported a method in which a strong low frequency electric field is applied to the FLC to 'straighten out' the chevron interfaces to induce quasi-bookshelf geometry. An oblique deposition technique has also been used to obtain bookshelf geometry (Johno et al. (1989) Jap. J. Applied Physics 28:L119). Bookshelf geometry in a SSFLC with a conventional rubbed polymer (e.g., polyvinyl alcohol, polyimide, etc.) alignment layer on the substrates was reported in U.S. Pat. No. 5,169,556. Researchers at Fujitsu first discovered a small number of naphthalene-based FLC materials which exhibited no chevron layer structures when introduced into a thin (several micron) SSFLC geometry. The smectic layers of these materials in the SmC* (chiral smectic C) phase formed the bookshelf geometry the SSFLC cell and the devices showed optical bistability. It was further reported that these compounds showed very little or no smectic layer thickness shrinkage at the SmA–SmC* transition or on further cooling into the SmC* phase. Layer shrinkage can be measured by observation of the layer spacing as a function of temperature using the well-known X-ray scattering technique, as described by Rieker et al. Phys. Rev. Lett. Vol. 59, 2658(1987). Bookshelf behavior was also discovered to occur in another small class of fluorinated FLCs, and optical bistability was also observed in FLC devices using these materials, as disclosed, for example, in U.S. Pat. No. 5,702,637.

Figure 1B:
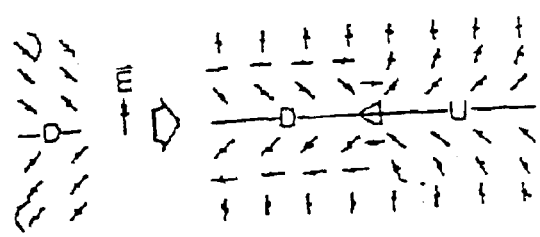
FIG. 1B is a schematic illustration of the bookshelf layer structure.

The term bookshelf is applied to liquid crystal layer geometry where in the idealized bookshelf geometry in the smectic C or smectic Car phase as illustrated in FIG. 1B the LC layers are perpendicular to the substrate walls and the long axes of the LC molecules are substantially normal to the LC layers. It will however be recognized by those of ordinary skill in the art, that some deviation from this ideal geometry can occur without significant loss of benefit. The bookshelf geometry facilitates true bistable switching of an SSFLC device with a steep transition and little or no hysteresis as illustrated schematically in FIG. 1B. Some deviation from the ideal geometry can occur without significant deterioration of bistable switching. In a practical sense, it is the substantial absence of chervon structure in the LC layer in the smectic C phase that is important for true bistable switching. Thus, a practical measure of the presence of the bookshelf geometry and the operational definition that will be used herein is bookshelf geometry that results in the substantial absence of chevron structure (e.g., by visual inspection as is known in the art). The term "quasi-bookshelf" layer geometry has also been used when the anomalous behavior of the bookshelf naphthalene compounds is discussed. The use of this term in the art may or may not refer to'the bookshelf geometry as intended herein as associated with chevron-free SSFLC devices. For example, Takanishi et al. (1990) Jap. J. Applied Physics 29(6):L984–986 used the term "quasi-bookshelf" to refer to naphthalene LCs that were chevron-free. In this case, "quasi-bookshelf" is the same as bookshelf as used herein. It will also be understood and appreciated in the art that the alignment layer and alignment method employed in an SSFLC cell may affect the quality of the bookshelf geometry. It should be noted that conventional rubbing methods employing polyvinyl alcohol can typically be employed to assess the presence of bookshelf geometry by visual inspection for chevrons. However, the term bookshelf as used herein is not intended to include induced bookshelf geometry as has been reported by W. Hartmann (1988) Ferroelectrics, Vol. 85, 67–77 or Johno et al. (1989) Jap. J. Applied Physics 28:L119.

For many applications of optical devices, an analog response to applied fields is highly desirable. Analog FLC devices are particular desirable because they have intrinsically fast switching characteristics. In this regard, researchers have engaged in a continuing search for materials that are useful analog FLC devices with limited success. As noted above, an analog effect called "thresholdless antiferroelectricity" or "V-shaped switching" has been described, exhibiting the highest analog susceptibility in FLCs to date. This behavior is known to occur in a class of FLCs which exhibit antiferroelectric phases. The effect has been described, for example, in LCs containing a 1-methylheptyloxy chiral tail or a 1-trifluoromethylheptyloxy chiral tail. The only known way to detect V-shaped switching and identify LC compositions that exhibit this behavior is the actual observation of the high susceptibility analog effect in an appropriately constructed FLC cell.

Figure 2A:
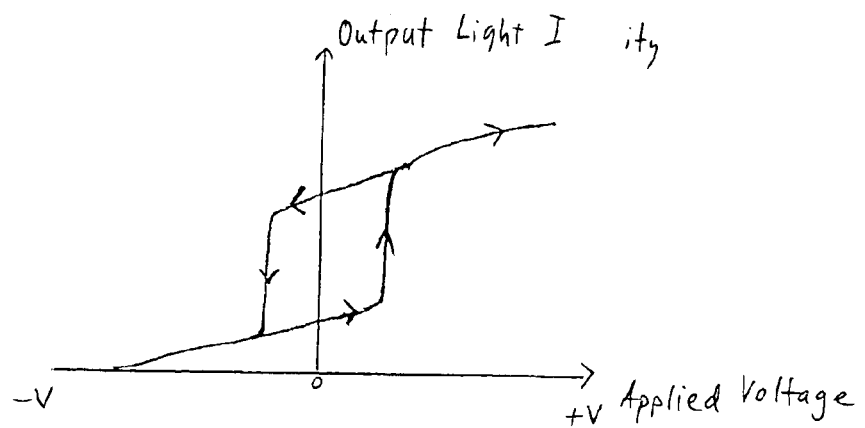
FIG. 2A is a schematic illustration of electrooptic response in a typically SSFLC bistable device.
Figure 2B:
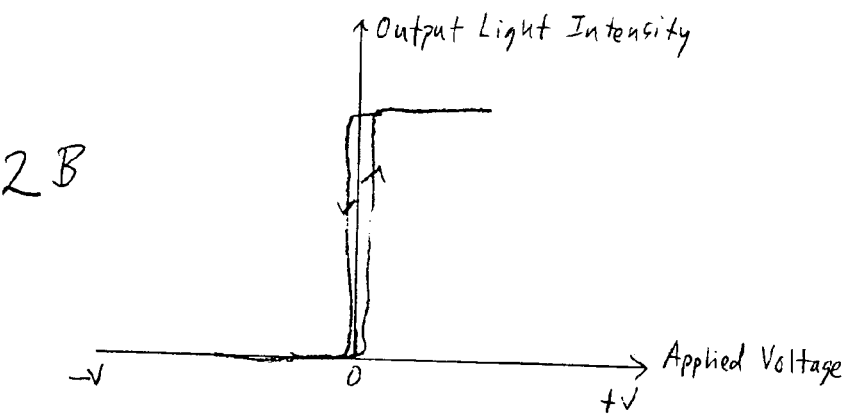
FIG. 2B is a schematic illustration of electrooptic response in a true bistable device with bookshelf layers.
Figure 2C:
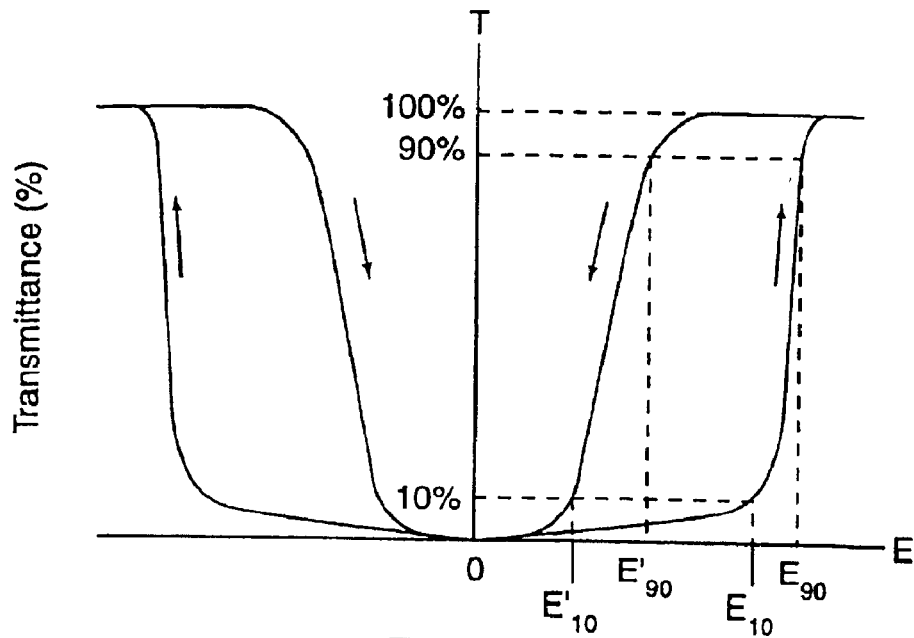
FIG. 2C is a schematic illustration of the electrooptic response of an antiferroelectric material from U.S. Pat. No. 6,057,007.
Figure 2D:
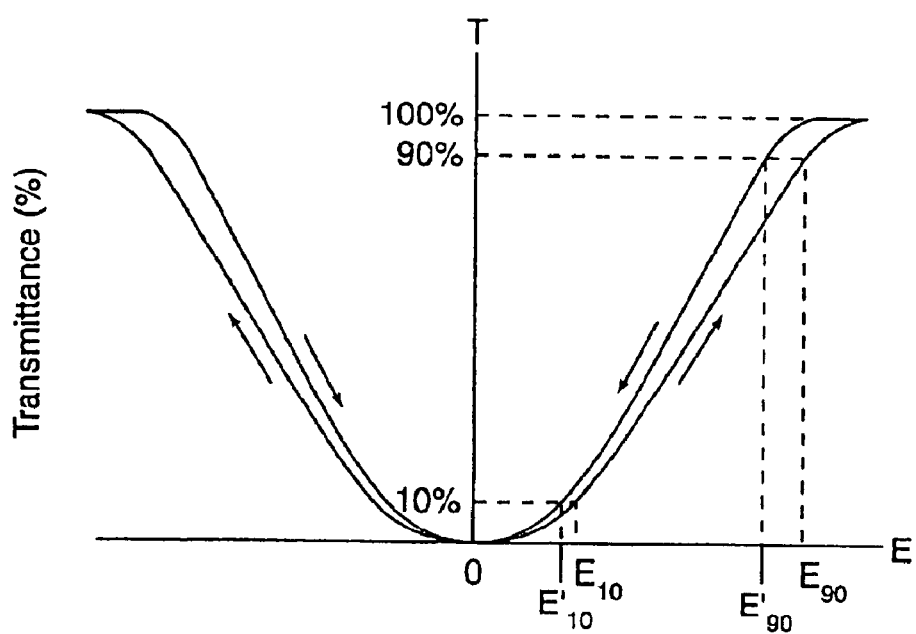
FIG. 2D is a schematic illustration of the electrooptic response of a V-shaped switching material from U.S. Pat. No. 6,057,007.

The term V-shaped switching is used herein as employed in P. Rudquist et al. (1999) J. Mater. Chem. 9: 1257–1261 to refer to a V-shaped electrooptical response and as illustrated schematically in FIG. 2D exhibiting very little or no hysteresis and very low or no threshold. In contrast the electrooptic response of an antiferroelectric material is illustrated in FIG. 2C. Those of ordinary skill in the art will appreciate that some deviation from an ideal V-shaped response with no measurable hysteresis or threshold can occur without significant loss of benefit.

It should be emphasized that both bookshelf geometry devices and V-shaped analog FLC devices at the time of this invention were know in the art to work only with a small number of specific FLC materials. There is no known correlation between compounds that exhibit bookshelf geometry and those that exhibit V-shaped switching and the structures of the different molecules seems to be completely disparate. It also should be noted that, in assessing the usefulness of FLCs, if any attention is paid to the material properties of the materials, it is paid to the properties of the materials in the working phase, i.e., the ferroelectric phase of the materials.

A liquid crystal material can typically exhibit several meso-phases on decreasing temperature from the isotropic liquid phase to the crystal phase, including a nematic phase, a smectic A phase, tilted smectic phases, such as a smectic C phase, and other higher ordered phases. Of particular interest to the current invention is the smectic A phase preceding (at higher temperature to) the tilted smectic C (or other tilted phases) ferroelectric phase.

For a conventional ferroelectric liquid crystal material, in the smectic A phase, the long axes of rod-shaped LC molecules are nominally perpendicular to the smectic layers and point along the layer normal. Upon cooling into tilted phases, for example, a smectic C phase, the molecules tilt and the thickness of smectic layers shrink. The anomalous behavior of the naphthalene bookshelf materials, which exhibit little or no shrinkage at this transition, was believed due anomalous thermal expansion of the materials (See, Takanishi et al. (1990) Jap. J. Applied Physics 29(6): L984–986 in which the observed lack of shrinkage is attributed to conformational change in the asymmetric molecules of the liquid crystal or to interdigitation of those molecules).

There is another type of smectic A phase that has been proposed by de Vries A., Mol. Cryst. Liq. Cryst., Vol. 41, 27(1977), ibid. Vol. 49, 179(1979), but which was never conclusively identified. In this type of smectic A phase, each individual molecule is not necessarily pointing along the smectic layer normal. Instead the long axis of each LC molecule, at any instant, makes an angle to the smectic layer normal. But because the LC molecules are randomly arranged, the average director of the LC molecules is pointing along the smectic layer normal, thus forming a smectic A phase. Such a smectic A phase is called a de Vries smectic A phase and it has the properties that is very different from a conventional smectic A phase.

The presence of a de Vries smectic A phase in a chiral liquid crystal material can be detected by infrared dichroism measurements. Liquid crystal molecules typically have at least one aromatic ring in the rigid core between flexible typically non-aromatic tails. The aromatic groups in the core absorb strongly in the infrared (IR), with an absorption strength that depends on the relative orientation of the polarization of the IR and the long axis of the liquid crystal molecule. Hence, the absorption is dichroic. In the de Vries smectic A phase, the molecules are all tilted away from the smectic layer normal, but are disordered azimuthally, so that the average long-axis direction is along the layer normal. Application of an electric field produces, as it does in all chiral smectic A phases, an electroclinic effect where the average molecular long-axis direction (the director) tilts away from the layer normal. In the ordinary smectic A case, this occurs without significant increase in the degree of azimuthal ordering, and hence the directionality of the IR dichroism of the material changes, but its strength does not. In the case of the de Vries Smectic A, the electroclinic effect is accompanied by an a typical increase in the azimuthal ordering which manifests itself as an increase in the difference between absorbance for IR light polarized parallel to the director and absorbance for IR light polarized perpendicular to the director. Thus, in a de Vries Smectic A material, the IR dichroism increases by an unusually large amount when the material is subjected to an applied (low-frequency) electric field.

The application of infrared dichroism measurement to the investigation of liquid crystal structure is well known in the art. A preferred method that can be applied to the infrared dichroism measurement is found in Hide, F.; Clark, N. A.; Nito, K.; Yasuda, A.; Walba, D. M. (1995) "Dynamic polarized infrared spectroscopy of electric field-induced molecular reorientation in a chiral smectic-A Liquid Crystal" Phys. Rev. Lett. 75, 2344–2347.

The following references describe the application of infrared dichroism measurements to liquid crystal materials: Blinov L. M. and Tournilhac, F. (1993) Molecular Materials 3(1):93–111; Ostrovskii, B. I et al. (1995) J. Physique II 5(7):979–1001; Kloepper, N. et al. (1997)) J. Physique 117(1):57–67; and Perova, T. S. et al. (1996) Ferroelectrics 180(1–4):105–115 (based on a paper given in July 1995 at the Int'l FLC Conference Cambridge, UK). Methods disclosed therein can also be employed in view of the teachings herein to detect the presence of a de Vries smectic A phase in LC and FLC materials.

The inventors have discovered that FLC materials that spontaneously form a bookshelf geometry and exhibit true bistable switching also exhibit a de Vries Smectic A phase. The presence of a de Vries Smectic A phase is, thus, an identifying characteristic of an FLC compound or material that will form the bookshelf geometry in an SSFLC device and exhibit true bistable switching. The presence of a de Vries Smectic A phase directly above the Smectic C phase in temperature in bookshelf forming FLCs is consistent with and explains the observation of little or no layer shrinkage on transition from the "Smectic A phase" to the Smectic C phase. Since de Vries Smectic A LC materials are already tilted in the Smectic A phase, these material exhibit very little or no smectic layer spacing change at the transition into the Smectic C phase (or on further cooling into the smectic C phase.) Little or no additional tilting occurs upon cooling of the material.

Two examples of ferroelectric liquid crystal compounds exhibiting a de Vries smectic A phase are compounds W399 and W415 whose structures are given in Scheme 7. Both of these compounds exhibit bookshelf geometry in an SSFLC cell. Compound W399 is discussed, for example, in Arnett, K. E. (1995) Mat. Res. Soc. Symp. Proc., 392:135. These compounds can be synthesized from materials disclosed in U.S. Pat. No. 5,543,078 in view methods disclosed therein and methods that are well known in the art of synthetic organic chemistry.

Another visual test is available for determining whether or not an FLC aligned in an SSFLC cell is in the bookshelf geometry. In this assay, which is described in Z. Zhuang (1991) Ph.D. Thesis "Surface Stabilized Ferroelectric Liquid Crystals" University of Colorado, Boulder Colo., a slow triangle wave (0.2 Hz) with DC balance is applied to the SSFLC cell with aligned FLC. The rubbed alignment layers of the cell may be parallel or antiparallel. The FLC is then observed the face of the FLC under microscope (app. 100×) on application of the triangle wave to the SSFLC cell. A plurality of pointed shapes or wedge-like shapes (which are described as "speed boats") are observed passing across the FLC. In a SSFLC cell that is not in the bookshelf geometry the shapes are all observed to travel in only one direction across the FLC with one polarity of the field. In an SSFLC in that is in the bookshelf geometry, the shapes are observed to travel in opposite directions away from each other across the FLC. This method can be used to determine whether or not a given FLC material aligned in an SSFLC exhibits bookshelf geometry. The method can be applied to individual compounds that are FLCs or to mixtures of compounds that are FLCs. Achiral or racemic LC materials can be tested for compatibility with bookshelf geometry by admixture with other LC materials, particularly those that are known to exhibit bookshelf geometry.

Scheme 8 illustrates generic structures of classes of LC molecules structurally related to the molecules W399 and W415. The methods disclosed herein can be applied specifically to the LC compounds of Scheme 8 to detect the presence of a de Vries smectic A phase or to detect the presence of bookshelf geometry in FLC mixtures containing one or more of the compounds of Scheme 8. The method can also be applied, among others, to the naphthalene-core LCs of U.S. Pat. No. 5,861,108, compounds disclosed in U.S. Pat. Nos. 4,886,619, 5,082,587, 5,399,291, 5,399,701, 6,019, 911 and 6,007,737, compounds having the cores of Scheme 6, compounds of the formula 3-2 in Scheme 3 and various swallow-tailed compounds known in the art.

Dimer liquid crystals are another class of liquid crystals that can be examined using the methods herein to detect the presence of a de Vries smectic A phase to ascertain which dimers will exhibit bookshelf geometry in SSFLC cells with appropriate alignment and V-shaped switching in analog cells. Of particular interest are liquid crystal dimers containing siloxane groups, such as those reported in U.S. Pat. No. 5,455,697 (incorporated by reference herein for the structures of the dimers therein.)

The inventors have also discovered that FLC materials exhibiting bookshelf geometry in SSFLC configurations exhibiting V-shaped switching behavior when introduced into FLC cells adapted for analog applications. Thus, any known FLC material that exhibits bookshelf geometry, e.g. the naphthalene-core compounds exemplified in U.S. Pat. Nos. 5,169,556 and 5,348,685, can be employed in FLC analog devices for V-shaped switching applications. More generally any chiral nonracemic LC compound or mixture of compounds that exhibits bookshelf geometry and true bistable switching in an SSFLC device will exhibit V-shaped switching in an appropriately adapted FLC device configuration. Thus, the assays disclosed herein for determining whether or not a given FLC compound forms a bookshelf geometry in an SSFLC device can also be used to identify LC molecules useful in V-shaped switching applications.

There are two formal possibilities regarding the particular FLC materials which are already known to exhibit V-shaped switching. It is possible that all of the known V-shaped materials are de Vries smectic A materials and further that all V-shaped materials that will be ever be identified will exhibit a de Vries smectic A phase, i.e., that the de Vries smectic phase is required in a V-shaped switching material. Alternative, it may be that only a subset of all V-shaped switching materials will exhibit a de Vries smectic A phase. The inventors currently believe that all V-shaped switching FLC materials will not exhibit a de Vries smectic A phase and thus that not all V-shaped switching materials will form a bookshelf structure in an appropriately treated SSFLC cell. However, if a V-shaped switching material does have a de Vries smectic A phase, then it will exhibit bookshelf geometry in an SSFLC device. Thus, a given V-shaped switching material can be screened by the methods disclosed herein for the presence of a de Vries smectic A phase to determine if that material will be useful in a bistable switching device.

Device configurations for SSFLC bistable operation and for V-shaped switching applications are generally known in the art and specific device configurations are disclosed in a number of the patent applications cited herein.

Given a material with a de Vries smectic A phase, an analog switching FLC device, which could be a V-shaped switching device, can be created as follows:

Two substrates, at least one of which is coated with polymer alignment layer (PVA, polyimide or other materials known in the art) and subsequently rubbed, are assembled to be parallel to form a liquid crystal cell. The gap of the cell is nominally thin and is typically less than 5 microns. The surfaces of the substrates are treated such that there is strong polar interaction, which in addition to proper choice of alignment materials, can also often be obtained by increasing the thickness of the alignment layer, between the surface and the ferroelectric liquid crystal. In such a device design, the easy axes of the treated substrates may be parallel and analog switching is obtained. Materials and methods for obtaining alignment layer thickness required to achieve an analog FLC device are understood and well-known in the art A number of the references cited herein refer to the formation of analog FLC devices and provide descriptions thereof. In some cases, in which a polyimide alignment layer is employed layer thickness is adjusted by selecting the concentration of the polyimide precursor in solvent. For example, a 4% by weight solution of polyamic acid in an appropriate solvent applied to cell substrate surfaces provides a sufficiently thick alignment layer for an analog cell. In general, an alignment layer thicker than about 500 Å should provide analog optical response.

Figure 3A:
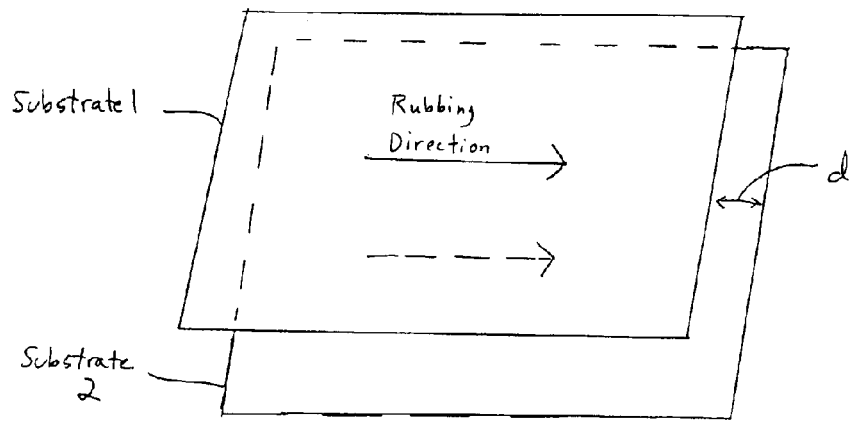
FIGS. 3A–3E illustrate analog device construction, where
Figure 3B:
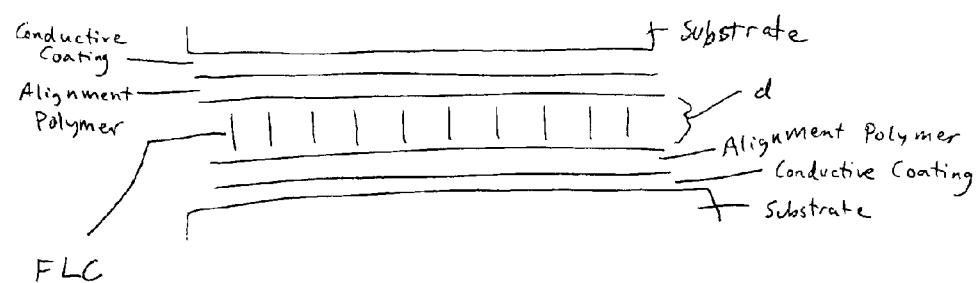
Figure 3C:
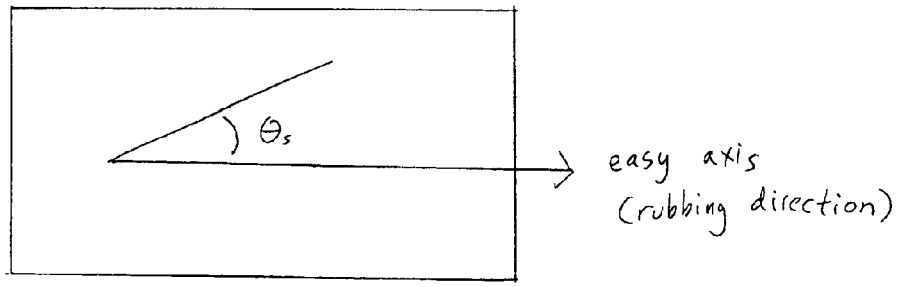
Figure 3E:
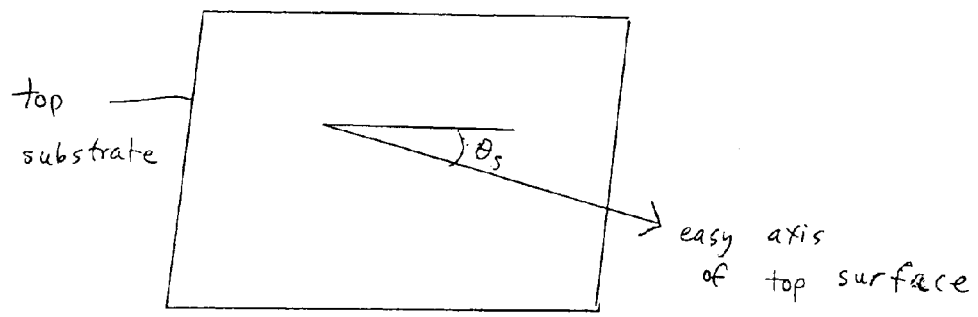
Figure 3E:
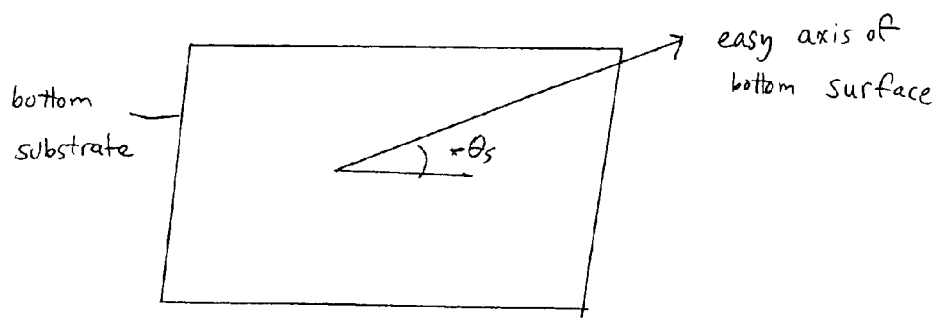
Figure 3D:
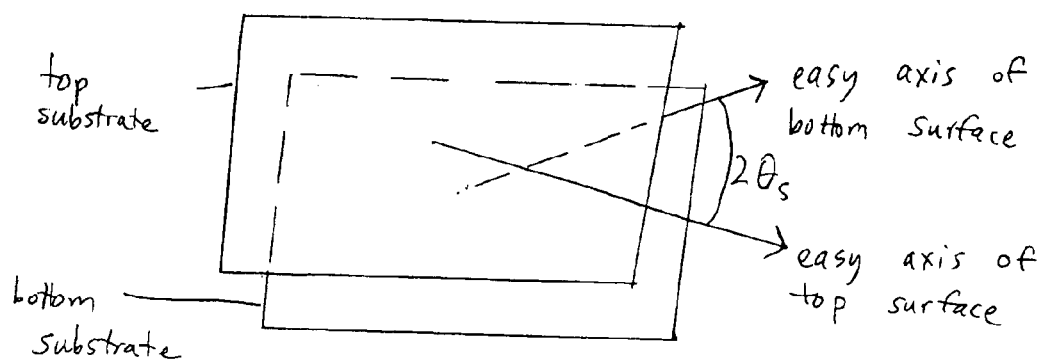

Analog switching devices of FLC materials with a de Vries smectic A phase can also be obtained in cross rubbed cells where the easy axes of the top and bottom substrates make an finite angle rather than being parallel. One such example is as follows. The strong surface interaction between the substrates and the FLC material, coupled with the large susceptibility of the FLC material, produces very large surface electroclinic tilt at the surface in the de Vries smectic A phase. This molecular tilt away from the easy axis at the surface can be measured optically. If the easy axes of the two substrates bounding the FLC is crossed by twice the surface electroclinic tilt angle, then the FLC molecules in the cell form a twisted structure and analog electrooptic switching of the device will be observed. Using such techniques, an FLC device containing W399 was shown successfully to display the analog switching behavior. The device construction in this case is sketched in FIG. 3A to 3E, where FIG. 3E illustrates the separated substrates of FIG. 3D to more clearly illustrate rubbing directions.

At a more fundamental level, V-shaped switching is found in cells with strong azimuthal and polar anchoring, and weak zenithal anchoring. These are conditions which may be realized as described above, for example.

The basic device construction for bistable switching devices is similar to the cell construction for analog and conventional FLC devices, that is, the device is composed of two substrates coated with polymers (PVA, polyimide and other materials known in the art) and treated with an easy axis each. The substrates are parallel and are separated with a spacing typically less than 5 microns. The easy axes of the substrates can be either parallel or making a finite angle (as discussed in Canon patent). At a fundamental level, bistable switching may be produced in cells by making the surface anchoring strong enough to give good alignment to FLC molecules but weak enough so that the FLC molecules near the surface participate in the switching process. At a more fundamental and scientific level, the surface interactions are such that the azimuthal anchoring may be overcome by other factors, including a very strong zenithal anchoring and very weak polar anchoring.

As is known in the art, weak surface anchoring arises when the substrates are treated with a thin alignment layer, when there is no insulating layer between the ITO electrodes and the polymer alignment layer, and often when the alignment polymer contains siloxane materials. Materials and methods for obtaining an alignment layer for a bistable SSFLC cell are understood and well-known in the art. In some cases, in which a polyimide alignment layer is employed layer thickness is adjusted by selecting the concentration of the polyimide precursor in solvent. For example, a 1% by weight solution of polyamic acid in an appropriate solvent applied to cell substrate surfaces provides a sufficiently thin alignment layer for a bistable cell. In general, an alignment layer thinner than about 200 Å should provide bistable optical response.

It should be understood that the only requirement for the FLC material described in this invention is that it possesses a de Vries smectic A phase above the smectic C* phase (or other optically tilted smectic phase). The other properties of the FLC material included in this invention may be tuned by mixing to provide preferred embodiments for either V-shaped or bistable cells.

All FLC materials that form bookshelf geometry in an SSFLC device possess a de Vries smectic A phase. According to this invention, FLC materials already discovered to show bistable electrooptic switching behavior, or the so-called bookshelf materials, can also be used to make analog switching FLC devices. Specifically, a cell containing the small class of naphthalene-based and fluorinated FLC materials as the liquid crystal media, when the substrates are treated properly, will also show analog switching behavior. Indeed, such behavior has been observed in a class of naphthalene based FLC materials when the thickness of the alignment layer of the substrates were increased, in accordance with this invention.

In contrast, all FLC materials that exhibit V-shaped switching may not a posses de Vries smectic A phase. However, the relatively small class of FLC materials containing 1-methylheptyloxy or 1-trifluoromethylheptyloxy chiral tails, which show V-shaped analog switching behavior, will exhibit bookshelf geometry in SSFLC device configurations and can be used to obtain bistable FLC devices, if the surface treatment is properly adapted as described above. Other FLC materials exhibiting V-shaped switching can be tested for the presence of a de Vries smectic phase. If the de Vries smectic A phase is present in the V-shaped switching material, then it will exhibit bookshelf geometry in SSFLC device configurations and can be used to obtain bistable FLC devices, if the surface treatment is properly adapted.

It is a practical observation in the art of FLC devices that smaller FLC material polarization favors a bistable electrooptic response, whereas for V-shaped analog switching, larger polarization is preferred. Thus efforts are made to reduce FLC spontaneous polarization in the naphthalene based and fluorinated FLC materials while the spontaneous polarization for the FLC materials containing the 1-methylheptyloxy or 1-trifluoromethylheptyloxy chiral tail remained high. According to the current invention, if by design the polarization of the current bookshelf material, containing the small class of naphthalene-based and fluorinated FLC materials, is increased, it will make it easier to obtain analog FLC devices using these improved FLC materials under the same conditions. Also according to the current invention, if by designing the FLC molecule, it is possible to obtain a new class of FLC materials with smaller spontaneous polarization containing the 1-methylheptyloxy or 1-trifluoromethylheptyloxy chiral tail. If this new class of material still have a de Vries smectic A phase, then the FLC device using this new class of FLC materials containing the 1-methylheptyloxy or 1-trifluoromethylheptyloxy chiral tail will have bistable electrooptic responses if the substrate surfaces are treated properly.

The occurrence of the valuable properties which are the subject of this invention may be tested without the necessity of creating either a V-shaped switching or optically bistable SSFLC cells. Nor is it necessary to make any measurements on the SmC* phase of the FLC material. Rather, a test for the presence of a de Vries Smectic A phase of the material is all that is needed to practice the invention.

Those of ordinary skill in the art will appreciate that materials and methods other than those specifically described herein can be employed in the devices and methods of this invention without undue experimentation. For example, any bistable and/or analog FLC device configurations known in the art can be employed with the de Vries smectic A materials of this invention. Any alignment method and or alignment materials known in the art to function for bistable FLC devices and V-shaped switching devices and readily available can be employed in this invention.

All references cited herein are incorporated in their entirety herein to the extent that they are not incompatible with the disclosure herein. In particular, references cited herein are incorporated by reference herein for their disclosure of the structures of bookshelf FLC materials, V-shaped switching materials, ferrielectric materials, thresholdless antiferroelectric materials, antiferroelectric materials and LC materials in general. Further, references cited herein are incorporated by reference herein for their descriptions of bistable and analog FLC cell configurations, alignment materials and methods, substrate materials and application of voltage to a bistable or analog cell to achieve the desired optical response.

Scheme 1

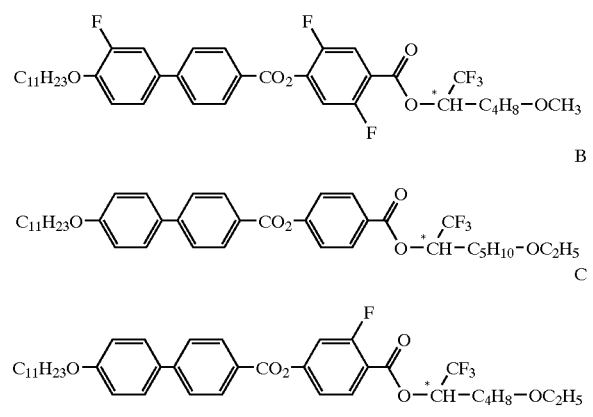

Scheme 2

From U.S. Pat. No. 6,057,007

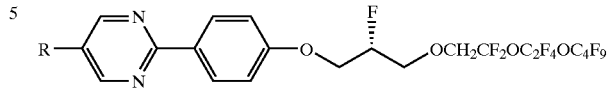

where R is $C_7H_{15}$ or $C_8H_{17}$

Scheme 3

3-1

From U.S. Pat. No. 5,728,864:

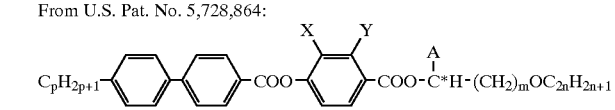

where A is —$CF_3$ or —$C_2F_5$, p is an integer ranging from 6–12,

X and Y are both H or one of X and Y is H and the other is F, and n and m are integers ranging from 2–4 and wherein the $C_pH_{2+1}$ group is linear Structurally related compounds include, among others:

3-2

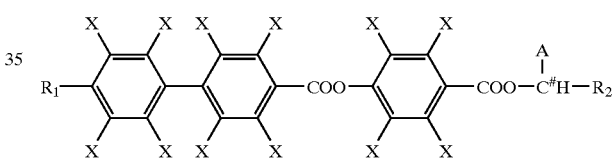

where A is —$CF_3$, —$CH_3$, —$C_2F_5$, —$C_2H_5$ or H and the carbon indicated with # may be asymmetric, each X, independent of other X's in the molecule can be H or F where there are a total of 1–6 F and preferably 1–3 F in the molecule, and $R_1$ and $R_2$, independent of each other, are alkyl, alkenyl, alkoxy, or ether groups having from 6–20 carbon atoms Scheme 4

From U.S. Pat. No. 6,002,042:

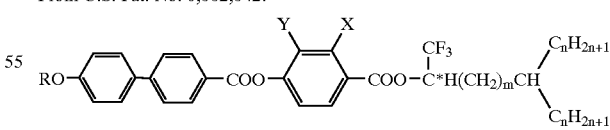

where * indicates an asymmetric carbon,

R is a linear alkyl group having 6 to 12 carbon atoms,

X and y are both H or one of X and Y is F and the other is H, m is an integer ranging from 0 to 5, and n is an integer ranging from 1 to 5

Scheme 5

From 5,938,973:

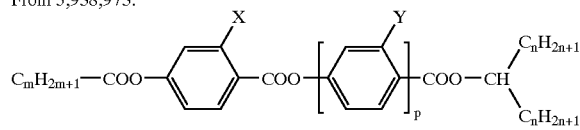

where m is an integer ranging from 4–10,
n is an integer ranging from 2–6,
p is 0 or 1,
X and Y independently are H or F From 5,976,409:

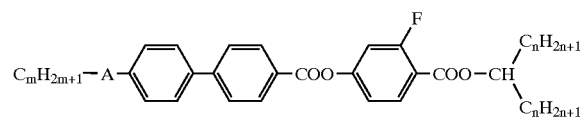

where A is O, COO or a single bond,
m is an integer ranging from 4–12, and
n is an integer ranging from 2–4

From 6,001,278:

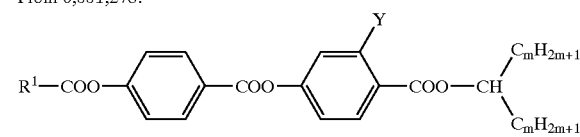

where R1 is a linear alkyl group having 4–10 carbons,
Y is H or F, and
m is 2 or 3

Scheme 6

Core Structures Related to Napthalenes

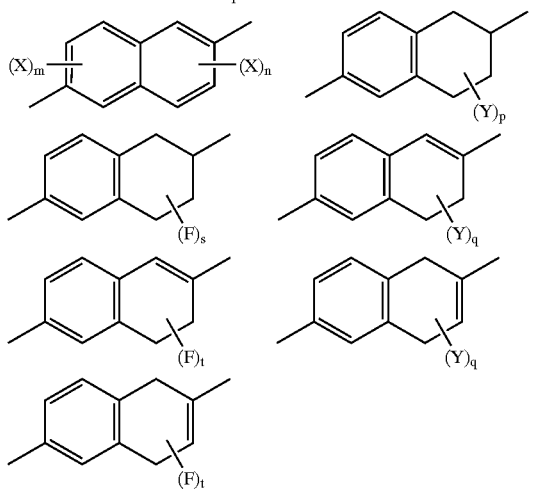

where X is F, —CH$_3$, —CF$_3$,
Y is —CH$_3$, or —CF$_3$,
n and m, independently are integers from 0–3,
p is an integer from 0–4,
q is an integer from 0–3,
s is an integer from 1–7, and
t is an integer from 1–6,

Scheme 7

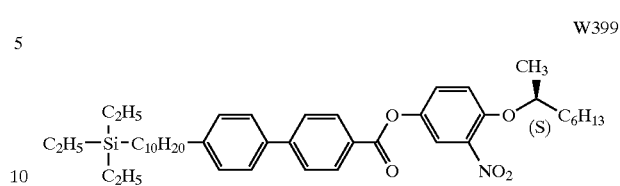

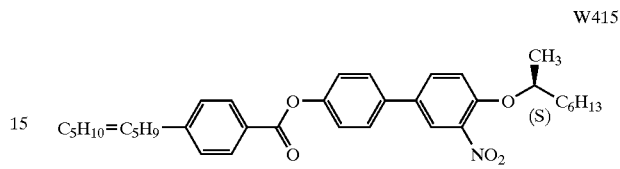

Both of these compounds exhibit a de Vries smectic A phase.

Scheme 8

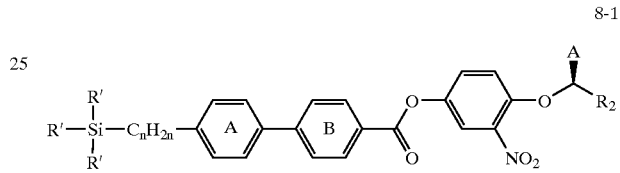

where A is F, —CH$_3$, —C$_2$H$_5$, —CF$_3$, or —C$_2$F$_5$,
n is an integer ranging from 6–12,
R' is a small alkyl group having from 1–6 carbons, particularly, —CH$_3$ or —C$_2$H$_5$,
R2 is an alkyl, fluoroalkyl, ether or fluoroether, and the A and B rings may each be substituted with one or two F

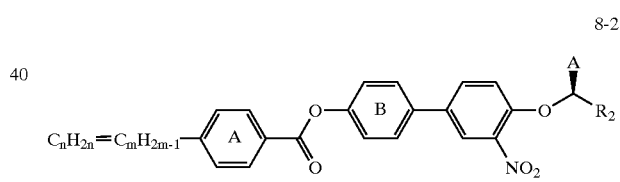

where a is F, CH$_3$, —C$_2$H$_5$, —CF$_3$, or —C$_2$F$_5$,
n and m are integers ranging from 1–12, particularly where n+m=6–12 and particularly where n=m,
R$_2$ is an alkyl, fluoroalkyl, ether or fluoroether, and
the A and B rings may each be substituted with one or two F

We claim:

1. A method for identifying a chiral nonracemic liquid crystal material useful in both bistable SSFLC devices and analog devices comprising determining the presence of a deVries smectic A phase in a chiral nonracemic liquid crystal, the presence of the phase being indicative of that the material will exhibit bookshelf geometry and V-shaped switching when introduced into the appropriate FLC device configurations, wherein infrared dichroism measurements are made to determine the presence of the de Vries smectic A phase.

2. The method of claim 1 wherein the chiral nonracemic liquid crystal material is a V-shaped switching material.

3. The method of claim 1 wherein the chiral nonracemic liquid crystal material is an antiferroelectric liquid crystal material.

4. The method of claim 1 wherein the chiral nonracemic liquid crystal material comprises a swallow-tailed liquid crystal.

5. The method of claim 1 wherein the chiral nonracemic liquid crystal material comprises a liquid crystal dimer.

6. The method of claim 5 wherein the dimer comprises a siloxane group.

7. The method of claim 1 wherein the chiral nonracemic liquid crystal material exhibits a tilted smectic phase.

8. The method of claim 7 wherein the chiral nonracemic liquid crystal material exhibits the phase sequence 1→SmA→SmC* and the smectic A phase is a de Vries smectic A phase over a useful portion of the SmA phase.

9. The method of claim 1 wherein the chiral nonracemic liquid crystal material exhibits a chiral smectic C phase.

* * * * *